United States Patent [19]

Landa et al.

[11] Patent Number: 5,044,755
[45] Date of Patent: Sep. 3, 1991

[54] PROBE FOR TRANSMITTING AND RECEIVING LIGHT FROM A SAMPLE

[75] Inventors: Isaac Landa, Potomac; Michael M. Anthony, Gaithersburg; George E. Toth, Colombia, all of Md.

[73] Assignee: LT Industries, Rockville, Md.

[21] Appl. No.: 318,245

[22] Filed: Mar. 3, 1989

[51] Int. Cl.⁵ .......................................... G01N 21/00
[52] U.S. Cl. .................................. 356/440; 356/73.1; 385/115
[58] Field of Search ............. 356/440, 244, 246, 73.1, 356/44, 409, 432, 436, 442; 350/96.13, 96.25; 250/227; 128/4, 6

[56] References Cited

U.S. PATENT DOCUMENTS

| | | | |
|---|---|---|---|
| 3,164,663 | 1/1965 | Gale | 356/436 |
| 4,286,881 | 9/1981 | Janzen | 356/440 |
| 4,444,516 | 4/1984 | Dostoomian et al. | 356/44 |
| 4,718,754 | 1/1988 | McIntosh | 356/73.1 |
| 4,852,962 | 8/1989 | Nicia | 350/96.13 |

Primary Examiner—Richard A. Rosenberger
Assistant Examiner—Hoa Pham
Attorney, Agent, or Firm—Sterne, Kessler, Goldstein & Fox

[57] ABSTRACT

A modular probe is provided to enable introduction of light to a sample to be analyzed by an electro-optical device. The probe of the present invention may include an optical rod or other device for propagating light, an optical barrel which in part surrounds the optical rod, and a sleeve which is provided to attach the probe to a source of light such as a fiber optical bundle. The probe may be fitted with a bidirectional focusing adapter and a reflective tip. A transverse probe is also described.

38 Claims, 2 Drawing Sheets

PROBE FOR TRANSMITTING AND RECEIVING LIGHT FROM A SAMPLE

BACKGROUND OF THE INVENTION

1. Field of the Invention

This invention relates generally to devices for receiving and transmitting light to a sample to be analyzed, and more particularly to a probe for use with a device for spectral analysis.

2. Background

There are a number of different devices which are used for rapid, accurate spectral analysis of the reflectivity, transmissivity or transflectance of samples. One of these devices, disclosed in U.S. Pat. No. 4,540,282 to Landa (the Landa patent), is a device which enables immediate and rapid analysis of a number of different products. This type of device can measure three generalized types of information: the chemical constituents of a sample; the physical constituents of a sample; and the quality parameters of a sample.

The chemical constituents of a product include such things as the octane number in gasoline or the amount of aromatics in gasoline. In another environment, such items as the amount of protein, starch, oil, and other characteristics of food may be measured. In yet another environment, such blood constituents as glucose or cholesterol can be measured using such a device. In the area of pharmaceuticals, the drug composition of a sample can be determined and such features as the active zones of drugs can be measured. In the tobacco industry, such chemical characteristics as nicotine, tar and methol can be measured using such a device.

The second broad type of characteristics which can be measured using such a device are called physical parameters. Such physical parameters include physical characteristics such as viscosity of liquids. In addition, characteristics such as molecular weight or the multilayer thickness of various coatings can be measured.

The third major area which can be measured using the device described in the Landa patent are quality parameters such as degree of bake. For example, it may be necessary to determine when a cookie is properly cooked. One can use the spectral response from the cookie in the process of it being cooked to determine when to stop cooking.

Another area in which quality parameters can be measured involves, for example, adhesive strength. Another example of how the device disclosed in the Landa et al. patent may be used is in determining the taste of beers or wines. Since each of these products has a spectral signature, it may be possible to determine the quality of a wine by comparing the spectral signature of that wine with a known product or standard. For example, once the quality of a particular wine is known, it may be possible to take a spectral signature of that wine and determine what spectral characteristic or signature other wines must have in order to similarly have a good taste. Thereafter, other wines need not be taste-tested in order to determine that they are good wines. A spectral analysis only need be done and the signature be taken in order to determine such characteristic.

As stated above, the device described by the Landa patent is capable of determining the spectral characteristics of a number of different products in a number of different forms.

There are basically three modes of introducing and detecting light from a sample. The first way is through reflectance. In the reflectance mode, light is introduced into a sample via a probe. Light is then reflected back to the probe and the probe relays this information to the instrument which analyzes the light return. Generally, this type of instrument will have a bidirectional fiber arrangement which enables light to move in two directions through the probe.

The second mode of operation is transmittance. In this mode, a first probe introduces light through a sample and the second probe will receive that light which has been transmitted through the sample. In this mode, two probes are necessary.

The third mode of operation is the transflectance mode. This mode is similar to the reflectance mode in that a bidirectional fiber is generally used which both transmits and receives light from the sample. In this mode, light is introduced to the sample. Light which is reflected from the sample is returned through the probe and transmitted back to the instrument for analysis. Light which transmits through the sample is reflected by a mirror back through the sample and again through the probe and on to the instrument for analysis.

For example, in order to obtain data for analysis, a probe may be inserted into a pipe to detect the constituents of a particular liquid product. If the probe is an optical rod surrounded by a sleeve, there can be a serious problem with introduction of liquid between the rod and the sleeve. This occurs if there are problems with the seal which is intended to prevent liquid from flowing between the rod and the sleeve. If such a problem occurs, the entire probe may need to be replaced. The reason that this is a serious problem is that each probe has particular characteristics. Therefore, by replacing one probe with another, the spectral signature which results may be altered as a function of the probe rather than a function of the material being analyzed.

Other probes in the art are made of a unitary structure. That is an optical bundle or the like may be surrounded by and epoxyed to a sleeve. Thus any failure in the optical bundle requires replacement of the entire probe. Since each probe has a distinct personality, the reliability of data is decreased. The above described unitary construction has an additional problem in that upon connecting the probe to a pipe or other body, a torque is normally required. If the probe is of unitary construction, any torque to the sleeve has a corresponding torque to the optical bundle. Such a torque can damage the probe thus causing additional delays and costs.

It is therefore an object of the invention to provide a probe which is modular.

It is a further object of the invention to provide a probe for introduction and receipt of light from a sample which is not sensitive to problems due to leaking.

It is yet a further object of the invention to provide a probe which may be used in solid samples such as cheese or meats or the like.

It is a further object of the invention to provide a probe which can be used in harsh environments, such as hydrofluoric acid, without adverse effects.

It is yet a further object of the invention to provide a probe in which the path length can be adjusted.

It is yet another object of the invention to provide a probe which does not necessitate the use of a separate and distinct mirror.

It is yet another object of the invention to provide a probe which has a bidirectional focusing capability to enable light passing through the probe to be focused onto optical fibers.

While the general concepts of the invention seeks to achieve the above stated objects, any individual embodiment may achieve these or other objects without varying from the invention.

SUMMARY OF THE INVENTION

In accordance with the purposes of the present invention as embodied and described herein, the present invention is a modular probe for use with an electro-optical device. Modularity allows for easy replacement of individual components of the probe without effecting the character of the probe. It also enables components which are susceptible to damage to be isolated from torque during installation in the environment in which the probe is to be used. The probe includes an optical rod which is sized to fit within an optical barrel. The optical barrel has attached thereto a sleeve which surrounds both the optical barrel and the optical rod. The optical rod, the optical barrel, and the sleeve are removably attached to form a modular probe.

A seal may be provided on the optical rod to prevent liquids from leaking through the probe.

The optical barrel may be provided for means to attach the probe to a tank or a pipe or the like. The barrel is also provided with a device for attachment to a fiber optic bundle.

In another aspect of the invention a reflective tip is provided to enable the probe to be used in a transflectance mode of operation, In yet another aspect of the invention, the probe includes a reflective tip which can be adjusted to vary the light path length of light traveling through the probe.

In yet another aspect of the invention a bifocusing adaptor is provided. The adaptor may include a focusing ball which focuses the light which both enters and exits the probe.

In another aspect of the invention, a transverse probe is provided in which light passing through the probe is orthogonally reflected.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE PREFERRED EMBODIMENTS

Figure 1:
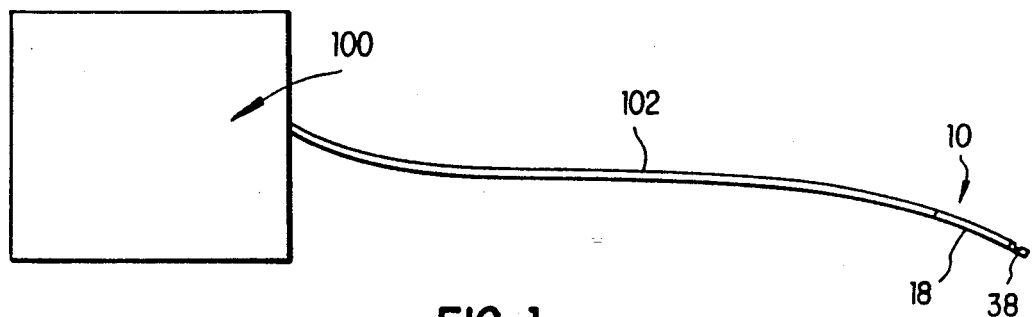
FIG. 1 is a schematic representation of the basic environment of the present invention.

Referring first to FIG. 1, a system is shown generally which utilizes an apparatus for optically analyzing a sample. This apparatus is shown schematically and labeled 100. An example of one apparatus 100 which is suitable for conjunction with the present invention is described in U.S. Pat. No. 4,540,282 to Landa et al. This patent is hereby incorporated by reference. The apparatus for optically analyzing a sample is an electrooptical system for rapid, accurate spectral analysis of the reflectivity or transmissivity of samples. A holographic diffraction grating is oscillated at high speeds to provide a rapid scanning of monochromatic light through a spectrum of wavelengths. The grating drive system may be an electrically driven mechanical oscillator which utilizes the back EMF of the oscillator motor to maintain oscillation at the desired amplitude and frequency. An optical shutter may be used to alternatively block the light entering the holographic diffraction grating as it is oscillated. The resultant dark period is utilized by the system to provide a reference offset value and to control cooling of the detectors. Source and exit optics are employed to optimally shape the light passing through the system. The Landa et al patent describes only one of the many devices which can be used with the invention. It is contemplated that many other devices cold be used in conjunction with the invention.

Light passes from and to a sample via a fiberoptic bundle 102. This bundle in turn is connected to a probe 12. It is this unique probe 12 which is the subject of the present invention. The probe enables a user to introduce light to a sample as will be described hereinbelow.

A. Modular Probe

Figure 2:
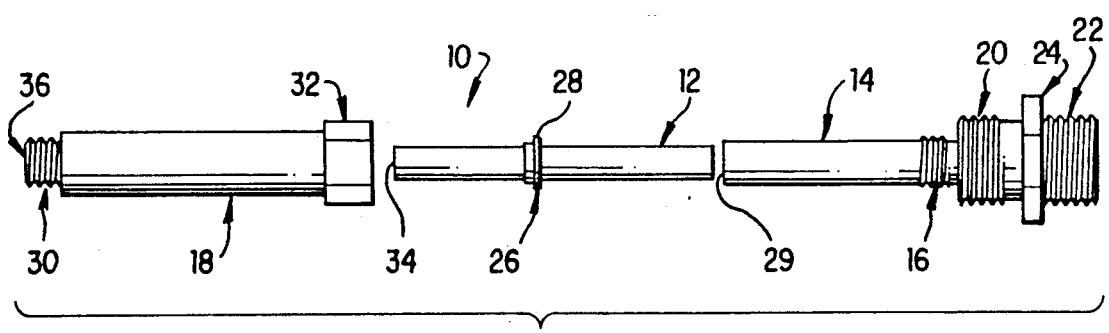
FIG. 2 is an exploded view of a probe of the present invention.

Referring to FIG. 2, one probe IO of the present invention is depicted. The probe shown in FIG. 2 is made up of four main component parts: an optical rod, an optical barrel, a sleeve and a seal. In a preferred embodiment these components are removeably interconnected in a modular manner as will be discussed below. The first component part is an optical rod 12 which is typically made of a solid sapphire or quartz rod. In addition to being a solid rod, it is possible that the optical rod 12 be made of a hollow tube. If a hollow tube is used as the optical rod 12, it is preferred that the internal surface of the rod be reflective.

If the optical rod 12 is a solid rod, light is introduced in a first end of the optical rod and will reflect down the length of the rod in a manner similar to fiberoptics.

The second component of modular probe 10 is an optical barrel 14 which defines a passageway or bore having a diameter approximately the same size as optical rod 12. The optical barrel 14 generally may have an internal surface to provide a sharp change in the coefficient of diffraction between the optical rod 12 and optical barrel 14. The optical barrel 14 includes sleeve threads 16 for attaching to a sleeve 18 which will be described in some detail below. In addition, optical barrel 14 has attachment threads 20 or similar attachment means for connecting the probe to a body 70 (see FIG. 5) which contains the sample to be analyzed. Because the optical barrel 14 and the optical rod 12 are not integrally connected, a torque may be introduced to the barrel without adversely effecting the optical rod 12 or the seal 26. When attaching the probe to a body a torque is introduced to the barrel. The modular concept prevents damage to the optical rod 12.

It is oftentimes necessary to analyze a liquid which is flowing through a pipe. In order to analyze such a fluid, a hole may be tapped into the pipe and the probe may be then inserted into the pipe and attached via attachment threads 20. Naturally, there may be many other ways to fix the probe into a pipe or the like. It should also be understood that the invention is not limited to the use of a probe to analyze liquids flowing through a pipe. The probe of the present invention may be used when analyzing virtually all liquids, solids or gases. In the embodiment of the invention shown in FIG. 2, the probe may be used either in a transmittance or a reflective mode. If used in a reflective mode, light passes through optical rod 12 and out the end 34 of the optical rod 12. The light is then reflected by the sample and passed back through optical rod 12 through a fiberoptic bundle to the apparatus for optically analyzing the sample. The fiberoptics generally have a connector thereon which is attached to the probe by the optic connector threads 22. This threading allows the fiberoptics to be attached and thereby light is introduced into the probe.

If the probe shown in FIG. 2 is used in the transmittance mode, a second probe which is similar to that of the one shown in FIG. 2 is used to receive light. In the transmittance mode, light is introduced through optic rod 12 and into and through the sample. The light which is transmitted through the sample is received by a second probe and the light is transmitted back to an apparatus for optically analyzing the sample.

The optical barrel 14 may also have a protruding nut surface 24 which is provided to assist removal from whatever the probe is attached to.

The third component of the probe of the present invention is a seal 26 which slides over the optical rod 12. This seal prevents liquid from flowing between optical rod 12 and optical barrel 14. While the seal may have a plethora of different embodiments, the seal of FIG. 2 utilizes a sealing surface 28 which extends outwardly from the body of seal 26. This seal is slidably mounted on optical rod 12 and is easily removable if desired. The seal 28 is compressed between a shoulder within sleeve 18 and end 29 of optical barrel 14. This enlarged part prevents liquid from flowing between optical rod 12 and optical barrel 14. To further prevent liquid from flowing between the optical rod 12 and the optical barrel 14, a rubbing compound may be put on the end of optical rod 12 to close up any gaps between the optical rod 12 and the optical barrel 14.

The seal may be an O-ring or may be configured as a body and a sealing surface 28 as shown in FIG. 2. There are a wide variety of seals that can be used depending on the application. For example, if the probe is to be used in a high temperature application, the seal may be made out of a ceramic. The seal may also be made out of a powder or a plastic. It could also be a swage.

The fourth component of the modular probe is a sleeve 18 which defines a hollow interior. This sleeve fits over optical barrel 14 which in turn fits over optical rod 12. The sleeve 18 has internal threads which enable optical barrel 14 to be attached thereto. The threads in sleeve 18 are complementary to sleeve threads 16 on the optical barrel 14. The optical sleeve may include tip threads 30 for attaching accessories such as a reflective tip (to be described later). In addition, the sleeve 18 has a protrusion 32 to enable easy disconnection of the sleeve 18 and the optical barrel 14.

When the four above-described components (the optical rod, the optical barrel, the sleeve, and the seal) are attached, the optical rod end 34 is flush with sleeve end 36. The optical rod 12 is inserted into optical barrel 14 which in turn is slid into sleeve 18. The seal 26 prevents fluid from flowing between the optical rod 12 and the optical barrel 14.

B. Reflective Tip for Use in Transflectance Mode

Figure 3:
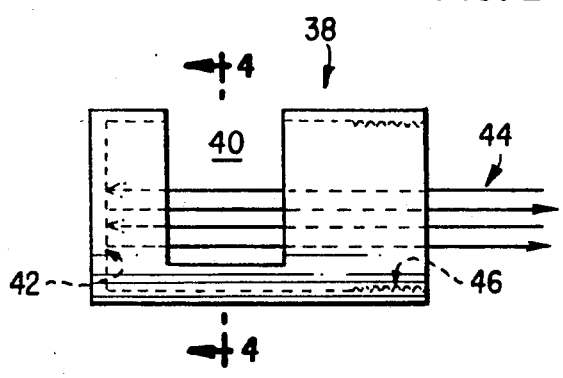
FIG. 3 is a side schematic view of a reflective tip of the present invention.
Figure 4:
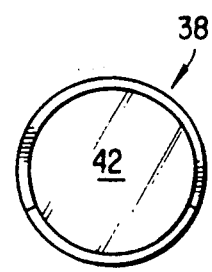
FIG. 4 is a cross-sectional view of the reflective tip cut along line 4—4 of FIG. 3.

In one embodiment of the invention, a reflective tip 38 may be used in conjunction with the other components of probe 10. Referring to FIGS. 3 and 4, a reflective tip shown generally as 38 is shown. This embodiment of the invention is used primarily when analyzing fluids. The reflective tip 38 is attached to the other components of the probe. In a preferred embodiment of the invention, the reflective tip 38 has internal threads 46 which are complementary to tip threads 30 on the sleeve 18. The reflective tip includes an opening 40 which allows fluids or gas to flow into the light stream 44. In this embodiment of the invention, the probe may be inserted into a stream of flowing liquid or the like. The light stream 44 travels through optical rod 12 and through the reflective tip 38. The reflective tip end 42 is reflective and thereby reflects the impinging light back through the sample. This process by which light is in part reflected by a sample, and is in part is transmitted through the sample is known as transflectance. The light which is transmitted through the sample is reflected by reflective surface 42 back through the sample. Thus, the light that comes out of probe 10 impinges on the sample, and is reflected back into the same probe, and the returning light is analyzed by the instrument 100 for optically analyzing a sample 10. Using this type of probe, a bidirectional fiber is used to transmit the light from the probe to the apparatus for optically analyzing a sample. In a bidirectional fiber photons flow down the fiber and photons come back through the fibers to the instrument 100.

The reflective surface 42 is generally a planar surface. In a preferred embodiment of the invention, it is the material which forms the reflective tip which has been polished. This material may be, for example, stainless steel or the like, depending on the particular application to which the reflective tip is to be used. While in the preferred embodiment of the invention it is the surface of the reflective tip 38 itself which is polished, it may be possible to have a separate and distinct mirror which is attached to the end of the reflective tip 38. A separate mirror, however, may not be suitable for all applications, since such a mirror would require an adhesive or the like to attach the mirror to the reflective tip. Therefore, it is preferred that the reflective surface 42 merely be a monolithic part of the reflective tip 38.

In one embodiment of the invention, reflective surface 42, rather than being a planar surface, may be concave. Since obtaining as much energy as possible through the system is critical, the use of a concave lens may help to enable more light to reflect back through the probe. If a reflective tip having a long path length is used, light reflecting off the planar surface may be lost. By using a concave surface, more of the light can be directed through the optical rod 12 and through the fiber optic bundles which link the probe to the apparatus for optically analyzing the sample 10. The dimensions of the concavity will depend in large part upon the sizing of the probe.

Part of the elegance of the present invention is its modularity. The fact that each of the components are individually replaceable helps to maintain the integrity of analysis. The fact that the seal is replaceable means that the user can replace a seal without disturbing the integrity of the remaining elements of the probe. As discussed previously, each probe has unique characteristics. For example, an individual reflective tip may have a character which, if replaced, will affect the future data as it relates to previous data. In other words, the character of the measurements is not affected by having to substitute one probe for another. If a seal is broken or defective, the sleeve 18 need only be disconnected from the optical barrel 14 and the seal 26 can then easily be removed. By doing this, the connection between the optical fibers and the optical barrel need not be disturbed. This is important, since the rotation of the fibers with respect to the sleeve can affect readings which are eventually analyzed by apparatus 10. Similarly, a rod can be replaced without disturbing the relationship between the optical fibers and the optical barrel 14. This enables reproducibility of test results and provides consistent results notwithstanding the replacement of a seal or an optical tube. Such reproduceability is critical, particularly when testing substances in which slight variations in the spectral signature can affect interpretation of data.

C. Adjustable Path Length Probe

It is anticipated under the present invention that the reflective tip 38 and the sleeve 18 be made of a single unitary construction. However, there are several advantages to making the reflective tip detachable from sleeve 18. By making the reflective tip 38 non-integral with sleeve 18, it is possible to make an adjustable path length probe. In other words, the length of the path can be adjusted simply by screwing or unscrewing the tip to a predetermined location.

Another advantage of having a removable tip is that different tips can be used without the need for an entire new probe.

Figure 5:
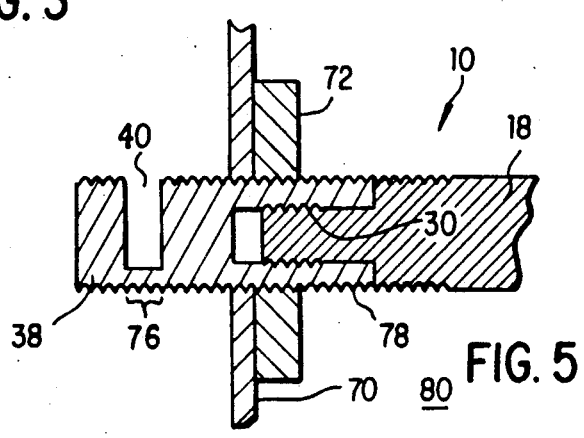
FIG. 5 is a cross-sectional view of one embodiment of the invention.

FIG. 5 shows another embodiment of the probe of the present invention. In this embodiment, a removable tip is used which enables components of a probe to be replaced without disrupting whatever I process is occurring in a pipe or vessel. For example, if a seal 26 in the probe is defective, it may be necessary to replace such a seal. The advantages of being able to replace a seal without replacing the entire probe have previously been described. However, in some applications it may be important not to disrupt the operation of whatever is being measured. For example, if the probe is used in a pipe which is flowing liquid under pressure, it may be extremely disruptive to shut down the operation of the pipe in order to replace the seal. In order to solve this problem, it may be possible to use the reflective tip as a seal in the opening of the pipe. Referring now to FIG. 4, such an embodiment is shown. In this embodiment, a vessel 70 defines an aperture in which probe 10 is inserted. In this embodiment, like embodiments previously described, sleeve 18 is attached to reflective tip 38 using threads 30. The outside surface of reflective tip 38 includes tip threads 78 which are sized commensurate with grooves or threads on the hole defined by vessel 70. The probe 10 can be unscrewed to a point that the opening 40 is blocked by vessel wall 70. If vessel wall 70 is thicker than the width 76 of opening 40, there will be no leakage out of the vessel. If, however, the vessel wall 70 is thinner than width 76 of opening 40, it may be necessary to include a built-up section 72 around the opening defined by vessel 70.

In this embodiment, a seal may be changed merely by unscrewing the probe to a point in which the gap is either blocked by the vessel wall 70 and built-up section 72, or on the outside of the vessel 80. The outside of the vessel is designated by the number 80 on the righthand side of vessel wall 70. Because the reflective tip 38 acts as a seal to prevent fluids within the vessel from escaping to the outside of vessel 80, the sleeve 18 may be disconnected from the reflective tip 38, thus enabling the user to replace the seal or the optical rod as necessary. This has the great advantage of being able to change either an optical rod or a seal without the need for shutting down operations of an entire plant or a portion of a plant which has liquid flowing through the particular pipe to which the measurements are taken.

D. Coated Optical Rod

Figure 6:
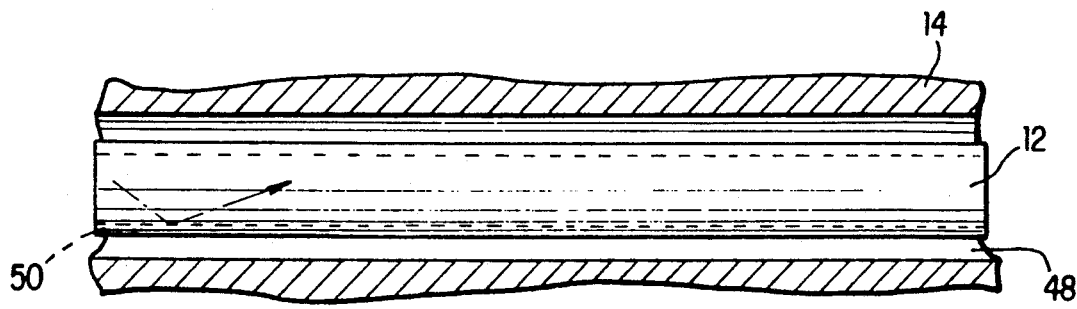
FIG. 6 is a schematic representation showing the embodiment of the invention using a reflective coating.

Turning now to FIG. 6, an embodiment of the invention is shown in which optical rod 12 has a coating 50. FIG. 6 shows a schematic view of the interface between optical barrel 14 and optical rod 12. Invariably, there will be a small spacing 48 between the optical rod and the optical barrel 14. If the probe is used to determine the characteristics of a liquid, it is possible that liquid may sometimes seep between the optical rod 12 and optical barrel 14 into spacing 48. If this occurs, two different problems may result. First, if the rod is being used in a harsh environment, such as hydrofluoric acid (HF), the rod can be severely affected by the acidity. To protect the rod from such harsh environments, it may be coated by various techniques with a heavy reflective metal such as gold or the like. The material may be coated by a conventional technique such as vapor deposition or the like. Naturally, any other inert coatings may also be used in conjunction with the invention.

Another advantage to coating the material is that if liquid is present in spacing 48, the optical characteristics of the optical rod may be changed. In other words, there will be behavioral changes of the spectrum as a result of seeing the spectral character of the liquid at the rod's surface or circumference. Thus, the functionality of the device is destroyed. By isolating the rod, by using a reflective coating, it does not matter that there is liquid which finds its way to the spacing 48.

E. Bidirectional Focusing Adaptor

In order to improve the efficiency of a probe, it is possible to add another modular unit to the invention. This unit, a bidirectional focusing attachment 54, is attached between the optical barrel 14 and the fiberoptics bundle. It may be, for example, attached to the optic connector threads 22 shown in FIG. 2. Corresponding threads 58 are the means by which this adaptor may be attached to the optical barrel 14. The bidirectional focusing attachment is de to focus light received by the probe through optical fibers and from the probe to the optical fibers. If the light emanating from the probe covers an area which is larger than the cross-section of a fiber, much of the light coming from the probe is lost. Since efficiency is extremely important, a bidirectional focusing attachment may enable more light to be received by the apparatus for optically analyzing the sample 10. The bidirectional focusing attachment receives light from modular probe IO and focuses it through focusing ball 68. This focusing ball is made of a material such as quartz or sapphire or the like. Adjustment rings 62 and 64 maintain the focusing ball 68 in a focused position. These rings may be moved in order to focus the focusing ball as desired.

F. Temperature Controlled Probe

In any of the above-described probe configurations, it may be necessary to have a sleeve with a controlled temperature. If, for example, temperature is a parameter which greatly affects the spectral fingerprint of a sample, it is important that the sample be maintained at a constant temperature during sampling. In order to control the temperature of the sleeve and the probe, electrical heaters are inserted into a sleeve holding the probe. These heaters maintain the temperature of the material being sampled at a constant.

G. Transverse Probe

Figure 7:
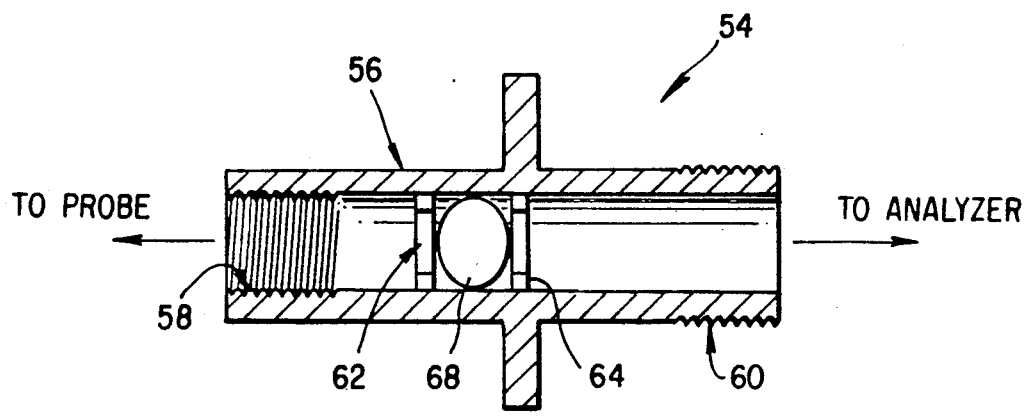
FIG. 7 is a schematic representation of a bifocusing adaptor embodiment of the invention.
Figure 8:
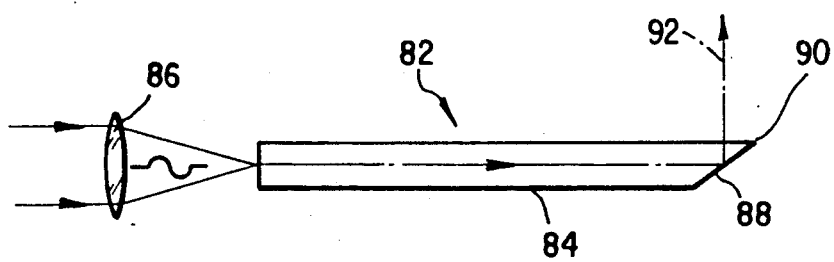
FIG. 8 is a schematic showing of a transverse probe of the present invention.

It is sometimes desired to analyze solid materials by use of an optical analyzing apparatus such as the one described in the Landa et al. patent. Since solid materials such as meat do not flow, unique problems arise. For example, the probe depicted in FIG. 3 may not be a preferred device for analyzing solid materials, since a solid material would not flow into opening 40. Therefore, a transverse probe such as that shown in FIG. 7 may be used. Referring now to FIG. 7, a transverse probe 82 is shown which has an optical rod 84 for transmitting light therethrough. The light is schematically shown by arrow 92. As shown in the schematic diagram, light may be introduced via a lens 86 into the optical rod 84. At the end of optical rod 84 is a mirror 88 which reflects light 86 in an orthagonal direction. Using this transverse probe, light passes down the optical rod 84 and is transmitted in a transverse direction as shown in FIG. 7. The point 90 of probe 82 may act as a knife to help insert the transverse probe 82 into the product to be sampled. Generally this type of probe may be used for non-Newtonian material such as meat, spongy materials, or the like. The light which is going in the transverse direction is then picked up by a second probe which transmits that light back to the apparatus for optically analyzing the sample.

The foregoing description of the preferred embodiments of the invention has been presented for purposes of illustration and description. It is not intended to be exhaustive or to limit it to the precise form disclosed. Obviously, many modifications and variations may be made in light of the above teachings.

The embodiments were chosen and described in order to best explain the principles of the invention and its practical application to thereby enable others skilled in the art to best utilize the invention in various embodiments and with various modifications as are suited to the particular use contemplated. As previously described, the invention may be used in a number of different environments, including solids, gases, and liquids. As such, each application may require somewhat different materials. For example, in an extremely harsh environment, the sleeve, that portion of the probe which is generally in most contact with the sample, may be made out of a material such as titanium or other heavy metal. Similarly, depending on the environment, the seal may be made out of a number of different materials and may be a number of different arrangements. Also, the degree of modularity may be increased by using, for example, two sleeves which interconnect rather than a single sleeve. Many other modifications and variations are contemplated without drifting from the spirit of the present invention. It is intended that the scope of the invention be defined by the claims appended hereto.

We claim:

1. A probe for use with an optical detection apparatus, comprising:
   (a) a sleeve defining a passageway;
   (b) an optical barrel having a bore extending along the longitudinal axis thereof, said barrel being at least in part removably inserted within the passageway defined by said sleeve;
   (c) a means for transmitting light, said means for transmitting light being at least in part removably inserted within the bore of said optical barrel;
   (d) means for introducing light to a sample through said means for transmitting light; and
   (e) a seal, said seal being disposed to inhibit the flow of liquid between said means for transmitting light and said optical barrel.

2. The probe as defined in claim 1, wherein said means for transmitting light is an optical rod.

3. The probe as defined in claim 2, wherein said optical rod is cylindrical.

4. The probe as defined in claim 2, wherein said optical rod comprises quartz.

5. The probe as defined in claim 2, wherein said optical rod comprises sapphire.

6. The probe as defined in claim 2, wherein said optical rod is coated with a reflective material.

7. The probe as defined in claim 6, wherein said reflective material is gold.

8. The probe as defined in claim 2, wherein said optical rod has a first end which is flush with a first end of said barrel.

9. The probe as defined in claim 2, wherein said seal is removably disposed around said optical rod and includes a sealing surface.

10. The probe as defined in claim 2, wherein said seal is an O-ring.

11. The probe as defined in claim 2, wherein said seal is a powder.

12. The probe as defined in claim 2, wherein said seal comprises a ceramic material.

13. The probe as defined in claim 2 wherein said seal is interposed between one end of said optical barrel and an interior shoulder within said sleeve.

14. The probe as defined in claim 1, wherein said means for transmitting light is a hollow cylindrical rod.

15. The probe as defined in claim 14, wherein the cylindrical rod defines a bore, the surface of which is substantially reflective.

16. The probe as defined in claim 2, wherein said optical barrel includes a means for connecting said optical barrel to a body.

17. The probe as defined in claim 16, wherein said optical barrel further includes a means for attaching a fiber optical bundle thereto for introduction of light into said optical rod.

18. The probe as defined in claim 17, wherein said optical barrel includes sleeve threads for removably attaching said sleeve.

19. The probe as defined in claim 1, wherein said sleeve includes means for removably attaching thereto a reflective tip.

20. The probe as defined in claim 19, further comprising a reflective tip removably attached to said sleeve.

21. The probe as defined in claim 20, wherein said reflective tip defines an opening for receiving a sample in the path of light passing through said means for transmitting light.

22. The probe as defined in claim 21, wherein said reflective tip has a reflective surface for reflecting light which has passed through a sample.

23. The probe as defined in claim 22, wherein said reflective tip is a monolithic member having a portion thereof polished to provide said reflective surface.

24. The probe as defined in claim 22, wherein said reflective surface is a mirror.

25. The probe as defined in claim 22, wherein said reflective surface is planar.

26. The probe as defined in claim 25, wherein said reflective surface is oriented perpendicular to light passing through said means for transmitting light.

27. The probe as defined in claim 25, wherein said reflective surface is concave.

28. The probe as defined in claim 22, wherein said reflective surface is oriented to reflect light back through the sample and through said means for transmitting light.

29. The probe as defined in claim 1, wherein said sleeve has integrally formed therewith a reflective tip.

30. The probe as defined in claim 29, wherein said reflective tip defines an opening for receiving a sample in the path of light passing through said means for transmitting light.

31. The probe as defined in claim 30, wherein said reflective tip has a reflective surface for reflecting light which has passed through the sample.

32. The probe as defined in claim 31, wherein said reflective surface is oriented to reflect light back through the sample and through said means for transmitting light.

33. The probe as defined in claim 1, further comprising a bidirectional focusing adaptor disposed at a location effective to focus light entering said means for transmitting light.

34. The probe as defined in claim 33, wherein said bidirectional focusing adapter comprises a focusing ball for focusing light passing into said means for transmitting light and for focusing light reflected back through said means for transmitting light.

35. The probe as defined in claim 34, wherein said focusing ball comprises quartz.

36. The probe as defined in claim 35, wherein said focusing ball comprises sapphire.

37. The probe as defined in claim 34, wherein said bidirectional focusing adapter further comprises adjustment rings for retaining said focusing ball.

38. A modular probe, comprising:
(a) an optical rod;
(b) a barrel for removably receiving said optical rod; and
(c) a sleeve for removably receiving said barrel and for removably attaching said sleeve to a body.

* * * * *